US00PP10435P

United States Patent [19]

Shaw

[11] Patent Number: Plant 10,435

[45] Date of Patent: Jun. 9, 1998

[54] STRAWBERRY PLANT 'DIAMANTE'

[75] Inventor: Douglas V. Shaw, Davis, Calif.

[73] Assignee: The Regents of the University of California, Oakland, Calif.

[21] Appl. No.: 747,406

[22] Filed: Nov. 12, 1996

[51] Int. Cl.[6] ..... A01H 5/00

[52] U.S. Cl. ..... Plt./49

[58] Field of Search ..... Plt./48, 49

*Primary Examiner*—James R. Feyrer

*Attorney, Agent, or Firm*—Burns, Doane, Swecker & Mathis, L.L.P.

[57] ABSTRACT

'CN210' is a new and distinct cultivar of strawberry plant of the day-neutral type which is more vigorous than 'Selva' or 'Seascape' and requires less chilling to maintain excellent fruit quality. When treated with appropriate planting regimes, 'CN210' has much larger fruit and produces greater yields than the comparison cultivars.

3 Drawing Sheets

FIELD OF THE INVENTION

This invention relates to a new and distinctive day-neutral type cultivar designated as 'CN210' also known as 'Diamante', which resulted from a cross performed in 1991 between advanced selections Cal 87.112-6 and Cal 88.270-1. The cultivar is botanically identified as *F.×ananassa* Duch.

'CN210' was first fruited at the University of California Wolfskill Experimental Orchard, near Winters, Calif. in 1992, where it was selected, originally designated Cal 91.248-6, and propagated asexually by runners. Following selection and during testing the plant of this disclosure was designated 'CN210'. With the decision that this plant was to be released, it was given the name 'Diamante' for the purposes of introduction into commerce and for international registration and recognition. Asexual propagules from this original source have been tested at the Watsonville Strawberry Research Facility, the South Coast Research and Extension Center, and to a limited extent in grower fields starting in 1994.

DETAILED DESCRIPTION OF THE INVENTION

Figure 1:
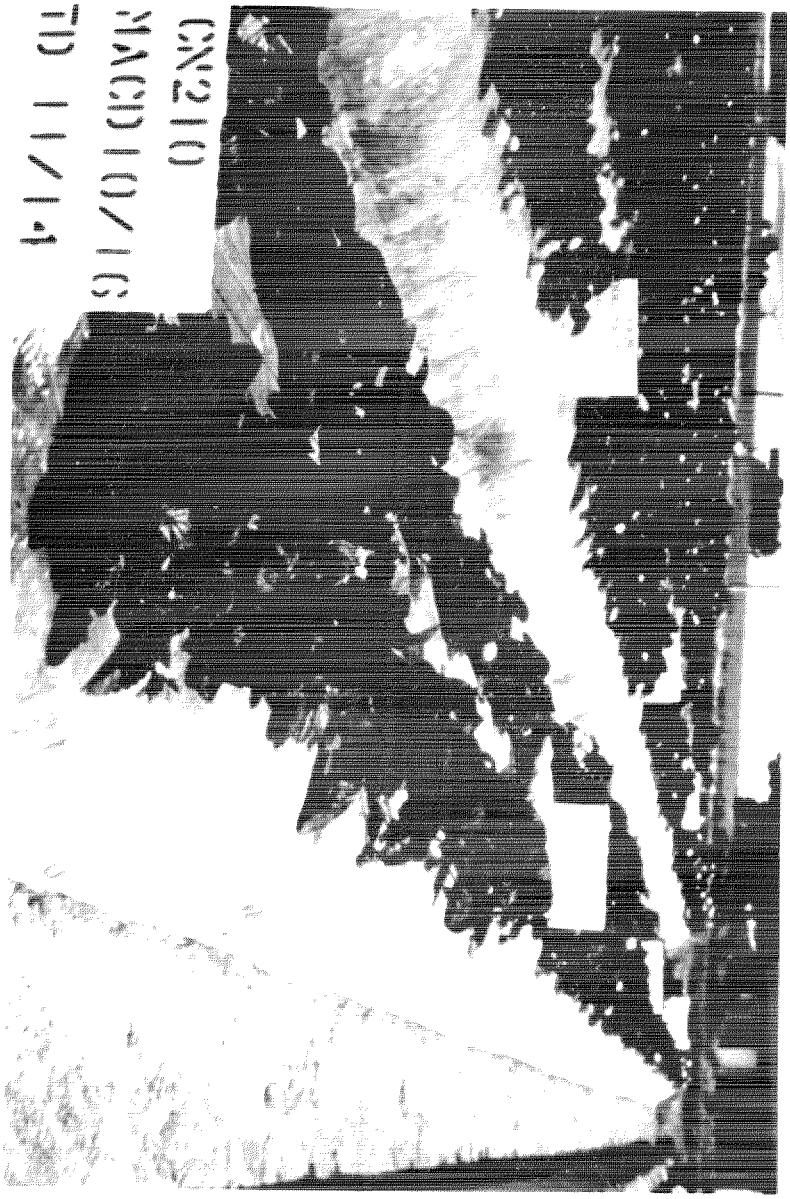
FIG. 1 depicts the general flowering and fruiting characteristics of the plant.
Figure 2:
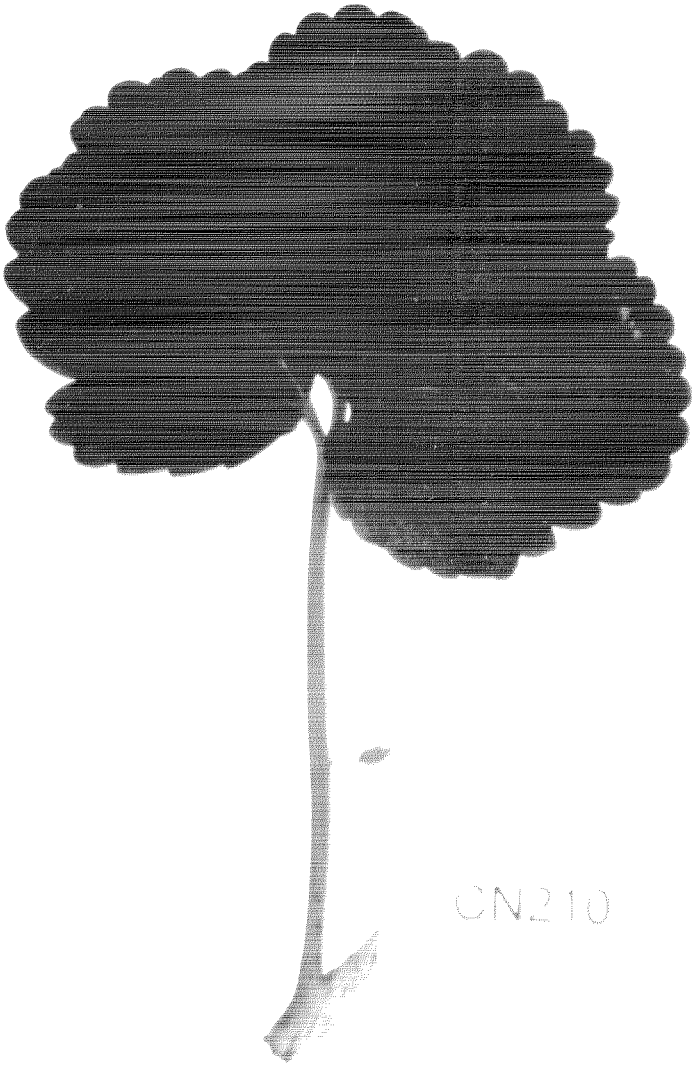
FIG. 2 depicts a typical mature leaf during late spring.
Figure 3:
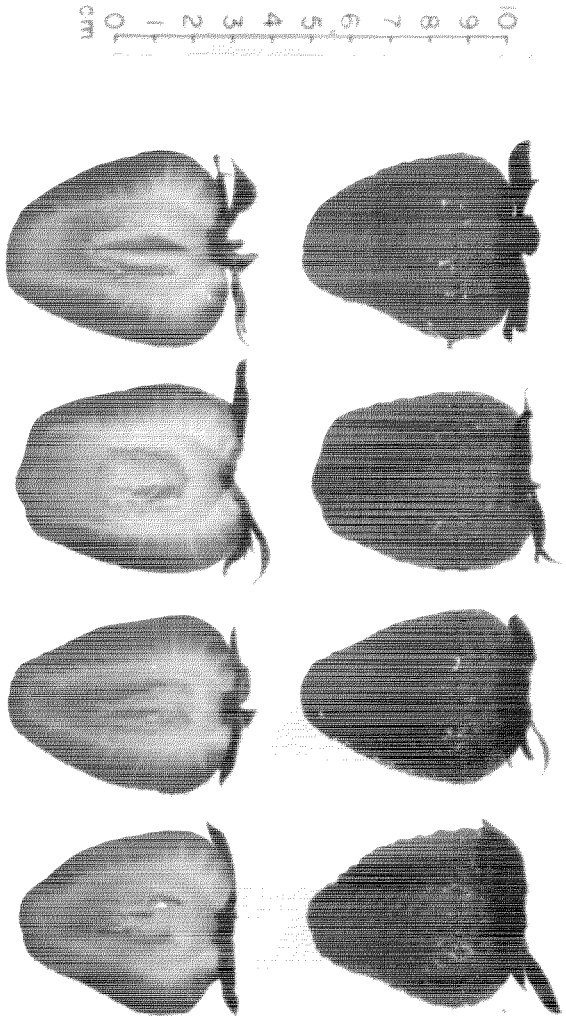
FIG. 3 depicts representative mid-season fruit.

'CN210' is moderate to weak in expressing the day-neutral character, being a stronger day-neutral than 'Seascape' (U. S. Plant Pat. No. 7,614), comparable or slightly more day-neutral than 'Selva' (U.S. Plant Pat. No. 5,266), and less so than 'Fern' (U. S. Plant Pat. No. 5,267) or 'Irvine' (U.S. Plant Pat. No. 7,172). The production pattern for 'CN210' is similar to that for 'Selva' or 'Seascape', and will be of special interest for winter plantings, where 'Selva' and 'Seascape' have been successful and summer plantings where 'Seascape', has been successful.

Plants and Foliage

Fruiting plants of 'CN210' are more erect and usually more vigorous than plants of 'Selva' or 'Seascape', but also are more open and compact. With appropriate treatment, plant size for 'CN210' is similar to 'Selva', and slightly smaller than 'Seascape'. Comparative statistics for foliar characters near mid-season are given for the three cultivars in Table 1. Leaflets are similar in size but substantially more rounded than leaves of 'Selva' or 'Seascape'. Leaves including petioles are somewhat shorter and broader than the comparison cultivars. Petioles are much thicker and more stiff than those of 'Selva' and 'Seascape'. 'CN210' has variable leaf convexity, generally more concave than leaves of 'Selva', and has fewer and more rounded serrations than the comparison cultivars. The adaxial (upper) leaf surface for 'CN210' is darker and more glossy than for 'Selva' and similar to 'Seascape', whereas the abaxial surface is slightly lighter than either comparison cultivar (Table 2).

Isozymes in Leaf Extracts

'CN210' has been classified for three isozyme systems using starch gel electrophoresis (Table 3): Phosophoglucoisomerase (PGI), Leucine Aminopeptidase (LAP), and Phosphoglucomutase (PGM). It is distinguishable from 'Selva' but not from 'Seascape' using this methodology. For electrophoretic procedures see: J. Amer. Soc. Hort. Sci. 106:684–687.

Disease and Pest Reaction

'CN210' is moderately susceptible to common leaf spot (*Ramularia tulasnei*), Verticillium wilt (*Verticillium dahliae*), and Anthracnose crown rot (*Colletotrichum acutatum*), and is relatively resistant to powdery mildew (*Sphaerotheca macularis*). When treated properly, it has tolerance to two-spotted spidermites (*Tetranychus urticae*) greater than 'Seascape' and 'Selva'. 'CN210' is tolerant to strawberry viruses encountered in California.

Flowering, Fruiting, Fruit, and Production Characteristics

'CN210' is similar to other California day-neutral cultivars (e. g. 'Selva' and 'Seascape') in that it will flower independently of day length, given appropriate temperature and fertility conditions. Comparative statistics for flower and fruit characters near mid-season are given for the three cltivars in Table 4. The primary flowers for 'CN210' are similar in size to 'Selva' and 'Seascape'; the sepals are somewhat smaller than for 'Seascape' and substantially larger than for 'Selva'. The calyx for 'CN210' varies from slightly indented to even, and each primary flower has 5–6 petals. The fruit shape for 'CN210' can vary but is typically a long rounded conic, and is easily distinguished from other California day-neutral cultivars. External and internal fruit color for 'CN210' are substantially lighter than for 'Selva' and 'Seascape', and fruit is substantially more glossy than either comparison cultivar (Table 2). Achenes vary from yellow to red, and are slightly indented.

'CN210' has been tested under a variety of cultural regimes, and optimal performance is obtained when nursery treatments and nutritional programs similar to those for 'Selva' and 'Seascape' are used. In general, 'CN210' is more vigorous than the comparison cultivars and requires less chilling to maintain excellent fruit quality. 'CN210' retains good fruit quality in summer planting systems, similar to 'Seascape'.

When treated with appropriate planting regimes, 'CN210' has much larger fruit and produces greater yields than 'Selva' or 'Seascape' (Table 5). Production for 'CN210' initiates at dates similar to the comparision cultivars and it produces slightly larger quantities of late-season fruit. Commercial appearance ratings have been superior to those for the comparison cultivars. Fruit firmness is similar to that for 'Selva' and greater than that for 'Seascape'. Subjectively, 'CN210' has excellent flavor, substantially better than 'Selva' or 'Seascape'. The fruit will be outstanding for both fresh market and processing, and will be useful for home garden purposes.

TABLE 1

Foliar characteristics for 'CN210', 'Selva' and 'Seascape'.

| Foliar | Cultivar | | |
|---|---|---|---|
| Character | 'Selva' | 'Seascape' | 'CN210' |
| Mid-tier leaflet | | | |
| Length (mm) | | | |
| mean | 72.6 | 72.8 | 64.9 |
| range | 65–88 | 65–82 | 57–72 |
| Width (mm) | | | |
| mean | 68.2 | 64.5 | 68.4 |
| range | 51–84 | 48–78 | 63–76 |
| Mid-tier leaf | | | |
| Length (mm) | | | |
| mean | 119.2 | 123.8 | 117.9 |
| range | 94–139 | 80–155 | 89–145 |
| Width (mm) | | | |
| mean | 130.1 | 127.1 | 124.7 |
| range | 111–170 | 108–150 | 115–139 |
| # leaflets/leaf | 3 | 3, rarely 4 | 3 |
| Leaf convexity | mostly flat to convex | concave to convex, mostly flat to convex | concave to convex, mostly flat |
| Serrations | | | |
| number | few-moderate | moderate | moderate |
| shape | round to semipointed | semiround to semipointed | rounded to semipointed |
| Leaf pubescence | moderate | moderate | moderate |
| Petiole pubescence | | | |
| density | heavy | mod. to heavy | heavy |
| direction | perpendicular | perp to slight acropetal | perpendicular |

TABLE 2

Foliar and fruit color characteristics for 'CN210', 'Selva', and 'Seascape'

| Color | Cultivar | | |
|---|---|---|---|
| Character | 'Selva' | 'Seascape' | 'CN210' |
| Leaf color (CIELAB) | | | |
| Adaxial | | | |
| L* | | | |
| mean | 31.9 | 29.1 | 30.4 |
| range | 30.2–33.7 | 26.9–32.3 | 28.4–32.1 |
| a* | | | |
| mean | −6.5 | −5.1 | −6.5 |
| range | −5.8—7.2 | −2.4—6.6 | −6.3—6.7 |
| b* | | | |
| mean | 12.7 | 11.3 | 11.1 |
| range | 9.8–15.8 | 9.5–16.5 | 9.7–14.0 |
| Munsell | 2.5G 3/3 | 2.5GY 4/3 | 2.5GY 5/5 |
| Abaxial | | | |
| L* | | | |
| mean | 48.3 | 48.3 | 50.3 |
| range | 47.2–50.4 | 47.0–49.6 | 48.8–51.7 |
| a* | | | |
| mean | −7.7 | −7.2 | −8.0 |
| range | −7.3—8.3 | −6.3—8.0 | −7.7—8.3 |
| b* | | | |
| mean | −17.9 | 18.1 | 18.2 |
| range | 16.7–19.4 | 16.7–19.0 | 16.0–19.6 |
| Munsell | 7.5GY 4/4 | 10GY 4/5 | 7GY 4/4 |
| Fruit color (CIELAB) | | | |
| External | | | |
| L* | | | |
| mean | 28.5 | 25.4 | 29.4 |
| range | 23.7–33.1 | 22.7–31.5 | 25.9–31.7 |
| a* | | | |
| mean | 29.7 | 28.7 | 36.2 |
| range | 26.9–31.5 | 25.4–33.1 | 32.8–39.2 |
| b* | | | |
| mean | 16.9 | 13.7 | 20.7 |
| range | 14.4–22.1 | 9.3–19.8 | 16.7–27.0 |
| Munsell | 5R 4/12 | 5R 3/7<br>5R 4/12 | 7.5R 5/13 |
| Internal | | | |
| L* | | | |
| mean | 48.8 | 45.5 | 61.2 |
| range | 44.4–53.1 | 38.3–55.0 | 52.6–66.2 |
| a* | | | |
| mean | 35.2 | 37.8 | 18.7 |
| range | 31.5–39.5 | 30.8–42.7 | 13.5–31.3 |
| b* | | | |
| mean | 29.4 | 26.9 | 16.4 |
| range | 26.9–33.9 | 21.9–34.2 | 13.4–24.6 |
| Munsell | 5R 5/13 | 7R 5/13 | 7.5R 8/6 |

*CIELAB is the abbreviation of the international color system known as "Commission Internationale De L'Eclairage" 1978. Recommendations on uniform color spaces -- color difference equations, psychometric color terms, Supplement No. 2 to CIE Publication No. 15. PARIS.-

TABLE 3

Isozyme phenotypes for 'CN210', 'Selva', and 'Seascape'.

| | Cultivar | | |
|---|---|---|---|
| locus | 'Selva' | 'Seascape' | 'CN210' |
| PGI | A2 | A4 | A4 |
| LAP | B3 | B3 | B3 |
| PGM | C2 | C2 | C2 |

TABLE 4

Flower and fruit characters for 'CN210', 'Selva', and 'Seascape'

| | Cultivar | | |
|---|---|---|---|
| Character | 'Selva' | 'Seascape' | 'CN210' |
| # petals | | | |
| mean | 5.8 | 6.1 | 5.1 |
| range | 5–8 | 5–7 | 5–6 |
| Flower position (relative to foliage) | even or interior | most even some interior or exposed | mostly exposed |
| Calyx diam. (mm) | | | |
| mean | 29.0 | 35.7 | 34.3 |
| range | 22–35 | 30–40 | 31–39 |
| Corolla diam. (mm) | | | |
| mean | 37.5 | 35.7 | 33.0 |
| range | 31–43 | 32–40 | 30–38 |
| Fruit shape length/width | | | |
| ratio | 1.16 | 1.15 | 1.18 |
| range | 1.02–1.25 | 1.00–1.31 | 1.11–1.32 |
| subjective | conic to flat conic | mostly sharp conic | mostly rounded conic |
| Calyx position | even with shoulder | even/slight neck | slight indent |

TABLE 4-continued

Flower and fruit characters for 'CN210', 'Selva', and 'Seascape'

| | Cultivar | | |
|---|---|---|---|
| Character | 'Selva' | 'Seascape' | 'CN210' |
| Seed position | even/slight extrude | slight indent to slight extrude | slight indent |

TABLE 5

Performance of 'CN210', 'Selva', and 'Seascape' evaluated at the Watsonville Research Facility in 1995 and 1996. All plants for these materials were harvested from Macdoel on October 16 or 17, and planted with three weeks supplemental storage prior to planting. Harvest was initiated in early April and continued through the first week of October. (52" 2-row beds, 17,300 plants/acre, 100 grams/plant = 316.3 crates/acre)

| Item | Yield (g/plant) | Late Yield (g/plant) | Appearance Score | Size (g/fruit) | Firmness |
|---|---|---|---|---|---|
| 'Seava' | 1,764 | 389 | 3.2 | 24.4 | 7.3 |
| 'Seascape' | 1,832 | 375 | 3.3 | 24.0 | 6.9 |
| 'CN210' | 2,035 | 440 | 4.1 | 30.7 | 8.1 |

Late yield includes harvest from August 20 through October 10.

When 'Diamante' is compared to 'Aromas' (U.S. Plant patent application Ser. No. 08/747,506, filed Nov. 12, 1996), it is found that 'Diamante' forms larger fruit that is lighter in coloration especially on interior fruit, and tends to be somewhat less productive.

I claim:

1. The new and distinct cultivar of strawberry plant substantially as herein described and illustrated.

* * * * *